(12) United States Patent
Gilbert et al.

(10) Patent No.: US 6,267,980 B1
(45) Date of Patent: Jul. 31, 2001

(54) DOSAGE FORMS AND USES

(75) Inventors: Julian Clive Gilbert; Andrew John McGlashan Richards, both of Cambridge (GB)

(73) Assignee: Darwin Discovery Limited (GB)

( * ) Notice: Subject to any disclaimer, the term of this patent is extended or adjusted under 35 U.S.C. 154(b) by 0 days.

(21) Appl. No.: 09/142,705

(22) PCT Filed: Mar. 11, 1997

(86) PCT No.: PCT/GB97/00674

§ 371 Date: Sep. 11, 1998

§ 102(e) Date: Sep. 11, 1998

(87) PCT Pub. No.: WO97/33570

PCT Pub. Date: Sep. 8, 1997

(30) Foreign Application Priority Data

Mar. 11, 1996 (GB) .................................................. 9605074

(51) Int. Cl.[7] ................ A61F 2/02; A61K 9/70; A61K 9/48; A61K 9/20

(52) U.S. Cl. .................... 424/424; 424/425; 424/443; 424/451; 424/464

(58) Field of Search ............................ 424/424, 425, 424/443, 451, 464

(56) References Cited

U.S. PATENT DOCUMENTS 5,204,116  4/1993  Edgren et al. .

OTHER PUBLICATIONS

Gupta, S.K. et al. (1996) Pharmacokinetics of Verapamil from an Osmotic System with Delayed Onset. Eur. J. Pharm. Biopharm. 42(1):74–81.

Primary Examiner—Carlos A. Azpuru
(74) Attorney, Agent, or Firm—Saliwanchik, Lloyd & Saliwanchik

(57) ABSTRACT

A pharmaceutical dosage form comprises, in a portion thereof, substantially single enantiomer (R)-verapamil and, in another, separate, portion thereof, substantially single enantiomer (S)-verapamil, wherein, in use, the different enantiomers are released at different rates from the dosage form.

24 Claims, 1 Drawing Sheet

DOSAGE FORMS AND USES

This application is a 371 continuation of PCT/GB97/00674 filed Mar. 11, 1997, which is a continuation of GB 9605074.5, filed Mar. 11, 1996.

1. Field of the Invention

This invention relates to verapamil and the discovery of novel pharmaceutical dosage forms thereof, and their use.

2. Background to the Invention

Verapamil (1) is presently in clinical use as a racemate and is used extensively for the treatment of hypertension. The opposite enantiomers of verapamil have different biological activities and different potencies. The pharmacological profile is determined by stereoselectivity of pharmacodynamics and pharmacokinetics. The (S)-enantiomer (levoverapamil) has the majority of the calcium channel antagonist activity (see DE-A-2059923), whilst the (R)-enantiomer (dexverapamil) differs in having greater sodium channel activity (see Bayer, Naunyn Schmiedeberg Arch. Pharmacol. (1975) 290: 81–97) and other cell-pump actions, in addition to higher bioavailability (plasma R:S ratio about 2.5), with slower clearance rate (plasma R:S ratio about 0.5). For the treatment of hypertension, the (S)-enantiomer may provide a safer treatment than the racemate, with an extended therapeutic window. The (R)-enantiomer may be of benefit for the reversal of multidrug resistance in cancer chemotherapy (see Eliason, Int. J. Cancer (1990) 46: 113); in this case hypotensive action by admixture with the (S)-enantiomer would be undesirable. Despite their different activities, it is conceivable that in some instances it may be advantageous to titrate the ratio of the two enantiomers to achieve a better therapeutic index.

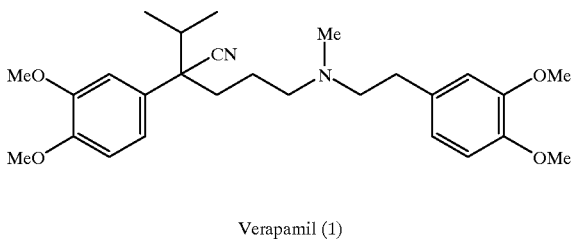

Verapamil (1)

Currently, verapamil is dosed as a racemic mixture both in immediate and controlled-release form, from which each enantiomer is released at the same rate. However, as reported by Longstreth in J.a. Clin. Pharmacol. (1993) 18 (2nd Edition): 315–336, the pharmacokinetic properties of each enantiomer are different, primarily due to differences in the rates at which they are metabolised. This has the effect that the ratio of the different enantiomers changes with time after initial dosing, which can lead to reduced efficacy of the drug. The actual enantiomeric ratio at any one time is dependent upon a number of factors and is complicated by the fact that different dosage forms provide different enantiomeric ratios.

SUMMARY OF THE INVENTION

According to the present invention, a pharmaceutical dosage form comprises, in one portion thereof, substantially single enantiomer (R)-verapamil and, in another, separate, portion thereof, substantially single enantiomer (S)-verapamil, wherein, in use, the different enantiomers are released at different rates from the dosage form.

The rates of release of the different enantiomers from the dosage form may be arranged such that their initial ratio, whether this is 50:50 or a non-racemic ratio, is maintained throughout the dosing period. By manipulating the administration of the different enantiomers in this way, presentation of the desired enantiomer to the target tissue is optimised, thereby increasing the clinical efficacy of the drug throughout the dosing period.

The present invention may also be beneficial if one of the enantiomers of verapamil is found to be responsible for causing an adverse side effect, as by altering the release from the dosage form of that enantiomer a significant reduction in that side effect may be achieved.

DESCRIPTION OF THE INVENTION

In the context of this Application, by substantially single enantiomer typically we mean that one enantiomer is in an excess of at least 70% by weight with respect to the other enantiomer, and is preferably in an excess of at least 80%, and more preferably 90%, or higher.

A number of different types of dosage form can be envisaged, for administration by a variety of routes, e.g. oral, rectal, transdermal, nasal, and ophthalmic.

One type of dosage form comprises a capsule containing two sets of multiparticulates having different release rates, one set containing (R)-verapamil and the other set containing (S)-verapamil. The multiparticulates themselves can be made by any of the conventional methods, including extrusion spheronisation, high shear granulation, non-pareil seeds, etc. The rates at which the different enantiomers are released from the multiparticulates can be achieved using any conventional controlled-release mechanism, for instance, matrix (ie. erosion diffusion), icoating, or osmotic. Dosage forms of this type are suitable for oral use.

Another type of dosage form comprises two tablets, i.e. as a combined product (kit), one tablet containing (R)-verapamil and the other tablet containing (S)-verapamil, the two tablets having different release rates. Again, conventional control-release technology can be used to achieve the desired effect. For example, two tablets having different release coatings or matrices may be used, or two osmotic pump tablets having different pumping rates. The tablets can then be administered in sequence, but preferably they are filled into a capsule for dosing simultaneously.

Another type of dosage form comprises an osmotic pump tablet comprising two distinct portions, typically two layers, one portion containing and pumping (R)-verapamil at one rate, and the other portion containing and pumping (S)-verapamil at another rate.

Another type of dosage form comprises a bi-layered tablet, one layer containing (R)-verapamil and the other layer containing (S)-verapamil, the two layers having different release rates for their respective enantiomers. Again, conventional control-release technology can be used to achieve the desired effect.

Another type of dosage form comprises a compressed coat tablet having a core containing one of (R)- and (S)-verapamil and, surrounding the core, a shell containing the other of (R)- and (S)-verapamil, the core and shell having different release rates for their respective enantiomers.

Another type of dosage form comprises a patch for placing adjacent a patient's skin, the patch comprising two distinct portions, one portion containing (R)-verapamil and the other portion containing (S)-verapamil, the two portions having different release rates for their respective enantiomers. Alternatively, two separate patches may be used, i.e. as a combined product (kit), one patch containing (R)

-verapamil and the other patch containing (S)-verapamil, the two patches having different release rates.

Another type of dosage form comprises a polymer implant comprising two distinct portions, one portion containing (R)-verapamil and the other portion containing (S)-verapamil, the two portions having different release rates for their respective enantiomers. Alternatively, two separate polymer implants may be used, i.e. as a combined product (kit), one implant containing (R)-verapamil and the other implant containing (S)-verapamil, the two implants having different release rates.

Another type of dosage form comprises an aerosol containing two sets of microparticles having different release rates, one set containing (R)-verapamil and the other set containing (S)-verapamil. Alternatively, two separate aerosols may be used, one for each enantiomer, i.e. as a combined product (kit), the microparticles of each aerosol having different release rates.

The dosage forms of the present invention may be designed to release either of the enantiomers faster than the other, depending upon the condition to be treated, or the patient type. It may be desirable to maintain a constant ratio of the separate enantiomers at the target tissue over a specified period of time, for instance at least 8 hours a day, preferably at least 12 hours a day, and most preferably 24 hours a day. The ratio maintained may be 50:50, or a non-racemic ratio in which either the amount of (R)-verapamil is greater than (S)-verapamil, or vice versa.

Another option would be to vary the ratio of the two enantiomers throughout the treatment period, or at least for a portion of that period. For instance, the release rate of either or both enantiomers can be arranged to vary, so that either the relative proportion of (R)-verapamil or of (S)-verapamil increases, or decreases, with time. The latter may be achieved, for instance, by using a number of different release coatings for the respective enantiomer.

The dosage forms of the invention may be used to beneficial effect in the treatment of conditions for which verapamil is usually administered, such as hypertension, angina, arrhythmia, atherosclerosis, migraine, glaucoma, stroke and cerebral ischemia, particularly in patients disposed to, or who may be put at risk by exposure to, an adverse side effect.

As, in the present invention, the two enantiomers are effectively dosed separately, it is essential that they are provided in a form that is not harmful to the prospective patient. If they are provided in salt form, both salts should preferably be stable and nonhygroscopic. Most preferably each enantiomer is in the form of its hydrochloride salt.

The present invention is now further illustrated by the following Example.

EXAMPLE
Preparation of Pellets by Extrusion/Spheronisation 9 g of powdered R-verapamil hydrochloride and 30 g Avicel PH101 (trade name) were blended together in dry form with a pestle and mortar. 16 g of water was slowly added, and mixed until thoroughly dispersed. The wet powder mass obtained was packed into the barrel of a ram extruder (25.4 mm in diameter) and extruded through a circular die, 1 mm in diameter and 4 mm long. The ram was attached to the crosshead of a physical testing instrument (Lloyds MX 50, Lloyds Instruments, Southampton, UK) which was operated at a rate of 200 mm/min. The extrudate was spheronised on a 12 cm diameter spheroniser (Caleva, Sturminister, UK) rotating at a speed of 1800 r.p.m. for 10–15 mins. The pellets produced were dried at 60° C. in a fluid bed drier.

Coating of Pellets
An aqueous dispersion of Surelease (Colorcon Limited, Orpington, UK) was applied to the pellets by spraying in a 3 inch (7.6 cm) Wurster column in a fluid bed coater (model Uni-Glatt, Glatt GmbH, Dresden, Germany) at a rate of 1.61 ml/min. Coatings of different thicknesses were applied as assessed on a weight-gain basis (ie. based on the weight of the uncoated pellets), in the range 1% to 16% gain in weight.

Pellets containing (S)-verapamil were prepared and coated in the same way.

The rate of drug release from the coated pellets was determined using a USP paddle method dissolution test procedure, with 1000 ml of distilled water and a paddle speed of 100 rpm at 37° C. Samples were taken continuously and fed through a flow-through cell in a Phillips PU8620 Tablet Dissolution System, to give an automatic absorption record at 230 nm of the dissolution of the drug (% dissolved) with time.

Figure 1:
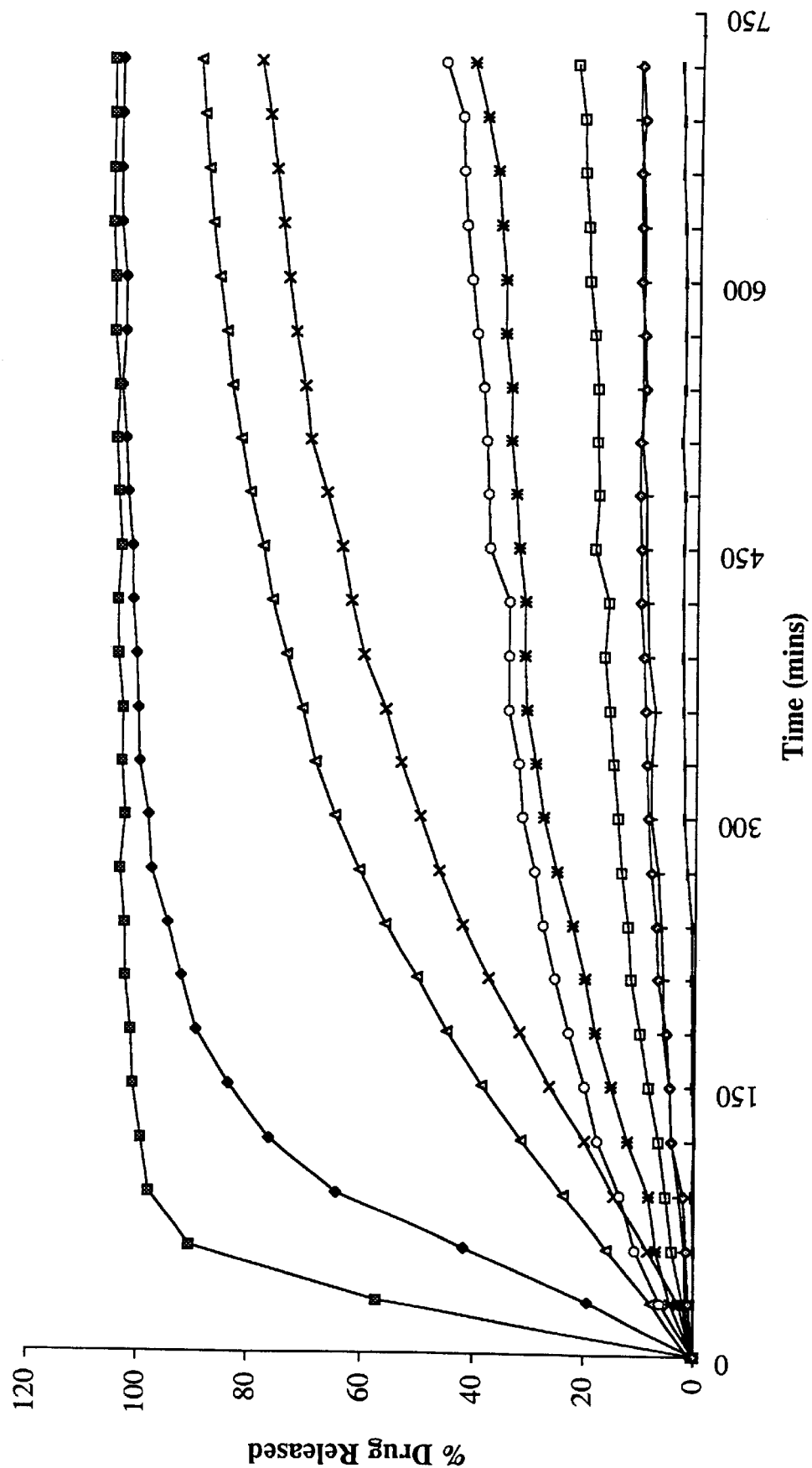
FIG. 1 is a graph showing the results of the dissolution tests carried out on each set of the coated pellets. In the key, below, TWG means total weight gain, and represents the weight gain of the pellet observed by application of the coating. The graph demonstrates that by altering the coating thickness different enantiomer release rates may be achieved. Therefore, both enantiomers can be formulated together, for sequential or simultaneous use, preferably for simultaneous use in the same formulation, to achieve different plasma concentrations of those enantiomers.

While the present Example is only on a small-scale, Newton et al, Int. J. Pharmaceutics (1995) 120: 95–99, disclose that formulations made on a small-scale will produce pellets on an industrial-scale e.g. in the range 20 g to 25 kg, and Fielden et al, Int. J. Pharmaceutics (1992) 81: 225–233, disclose that similar formulations will function on a small-scale ram extruder and on an industrial-scale cylinder extrudate.

Key
—◆—S-verapamil-1% TWG
—⊞—R-verapamil-1% TWG
—▲—S-verapamil-2% TWG
—✳—R-verapamil-2% TWG
—✱—S-verapamil-4% TWG
—○—R-verapamil-4% TWG
—+—S-verapamil-8% TWG
—⊟—R-verapamil-8% TWG
——S-verapamil-16% TWG
—◇—R-verapamil-16% TWG

What is claimed is:

1. A pharmaceutical dosage form comprising in one portion thereof substantially single enantiomer (R)-verapamil and in another, separate, portion thereof substantially single enantiomer (S)-verapamil, wherein, in use, the different enantiomers are released at different rates from the dosage form.

2. The dosage form according to claim 1, wherein the release rates of the different enantiomers are selected to give a substantially constant ratio of those enantiomers at a target tissue for at least 8 hours in a day.

3. Dosage form according to claim 2, wherein the ratio of the enantiomers at the target tissue is about 50:50.

4. The dosage form according to claim 2, wherein the ratio of the enantiomers at the target tissue is a non-racemic ratio, with (R)-verapamil being in excess compared with (S)-verapamil.

5. The dosage form according to claim 2, wherein the ratio of the enantiomers at the target tissue is a non-racemic ratio, with (S)-verapamil being in excess compared with (R)-verapamil.

6. The dosage form according to claim 1, wherein at least the release rate of one of the enantiomers varies with time.

7. Dosage form according to claim 6, wherein the rate of release of (R)-verapamil increases or decreases with time.

8. The dosage form according to claim 6, wherein the rate of release of (S)-verapamil increases or decreases with time.

9. The dosage form according to claim 1, from which (R)-verapamil is released faster than (S)-verapamil.

10. The dosage form according to claim 1, from which (S)-verapamil is released faster than (R)-verapamil.

11. The dosage form according to claim 1, which comprises a capsule containing a plurality of first particles containing (R)-verapamil and a plurality of second particles containing (S)-verapamil, the first and second particles having different release rates for their respective enantiomers.

12. The dosage form according to claim 1, which comprises a first tablet containing (R)-verapamil and a second tablet containing (S)-verapamil, the first and second tablets having different release rates for their respective enantiomers.

13. The dosage form according to claim 12, wherein the first and second tablets are enclosed within a capsule.

14. The dosage form according to claim 1, which comprises an osmotic pump tablet having a first portion containing (R)-verapamil and a second portion containing (S)-verapamil, wherein the first and second portions have different pumping rates for their respective enantiomers.

15. The dosage form according to claim 1, which comprises a bi-layered tablet, one layer containing (R)-verapamil and the other layer containing (S)-verapamil, the two layers having different release rates for their respective enantiomers.

16. The dosage form according to claim 1, which comprises a compressed coat tablet having a core containing one of (R)- and (S)-verapamil and, surrounding the core, a shell containing the other of (R)-verapamil and (S)-verapamil.

17. The dosage form according to claim 1, which comprises a patch for placing adjacent a patient's skin, the patch comprising a first portion containing (R)-verapamil and a second portion containing (S)-verapamil, the first and second portions having different release rates for their respective enantiomers.

18. The dosage form according to claim 1, which comprises two patches, each for placing adjacent a patient's skin, one patch containing (R)-verapamil and the other patch containing (S)-verapamil, the two patches having different release rates.

19. The dosage form according to claim 1, which comprises a polymer implant having a first portion containing (R)-verapamil and a second portion containing (S)-verapamil, wherein the first and second portions have different release rates for their respective enantiomers.

20. The dosage form according to claim 1 comprising two polymer implants, one implant containing (R)-verapamil and the other implant containing (S)-verapamil, the two implants having different release rates.

21. The dosage form according to claim 1, which comprises an aerosol containing two sets of microparticles having different release rates, one set containing (R)-verapamil and the other set containing (S)-verapamil.

22. The dosage form according to claim 1, which comprises two aerosols, one containing microparticles containing (R)-verapamil and the other containing microparticles containing (S)-verapamil, the microparticles in the two aerosols having different release rates for their respective enantiomers.

23. A method for treating a condition in a patient, said method comprising administering a pharmaceutical dosage form of substantially single enantiomer (R)-verapamil and substantially single enantiomer (S)-verapamil as defined in claim 1, wherein said condition is selected from hypertension, angina, arrhythmia, atherosclerosis, migraine, glaucoma, stroke and cerebral ischemia.

24. The method according to claim 23, wherein said patient is disposed to an adverse side effect.

* * * * *

UNITED STATES PATENT AND TRADEMARK OFFICE
CERTIFICATE OF CORRECTION

PATENT NO.    : 6,267,980 B1
DATED         : July 31, 2001
INVENTOR(S)   : Julian Clive Gilbert, Andrew John McGlashan Richards It is certified that error appears in the above-identified patent and that said Letters Patent is hereby corrected as shown below:

<u>Column 4,</u>
Line 62, "Dosage" should read -- The dosage --.

<u>Column 5,</u>
Line 7, "Dosage" should read -- The dosage --.
Line 39, "(5)" should read -- (S) --.

Signed and Sealed this

Twenty-sixth Day of February, 2002

*Attest:*

*Attesting Officer*

JAMES E. ROGAN
*Director of the United States Patent and Trademark Office*